US00PP08169P

United States Patent [19]

Friday

[11] Patent Number: Plant 8,169

[45] Date of Patent: Mar. 9, 1993

[54] P.F. 17 PEACH TREE

[76] Inventor: Paul J. Friday, P.O. Box 850, Coloma, Mich. 49038

[21] Appl. No.: 726,320

[22] Filed: Jul. 5, 1991

[51] Int. Cl.[5] ..... A01H 5/00
[52] U.S. Cl. ..... Plt./43.2
[58] Field of Search ..... Plt. 43.2

*Primary Examiner*—James R. Feyrer
*Attorney, Agent, or Firm*—Fred P. Kostka

[57] ABSTRACT

A new and distinct variety of peach tree having the following unique combination of desirable features:

1. Producing a very firm fruit having a resilient flesh texture.
2. Blossoms are partially non-showy when in full bloom.
3. A substantially spheroidal fruit with an attractive red skin coloring over a majority of the surface.
4. A late maturing fruit of good taste.
5. A late maturing (after maturity of Redhaven peach) fruit of good storage and shelf life.

2 Drawing Sheets

ORIGIN OF VARIETY

The new variety of peach tree (hereinafter referred to as the P.F. 17 peach tree) was originated by Paul Friday in the experimental orchard maintained for the purpose of breeding of Paul Friday Farms Inc., located in Coloma, Mich. Coloma is located in the southwest section of Michigan. The P.F. 17 peach tree was developed in a first generation cross between two seedlings.

The female parent and the male parent are each deliberately selected ones of peach trees of unknown origin grown in the experimental peach tree breeding orchard of the Paul Friday Farms Inc. The male and female seedling were grown at the Paul Friday Farms Inc.

ASEXUAL REPRODUCTION OF THE VARIETY

The new and distinct variety of peach tree was asexually propagated by budding as performed in the experimental orchard of Paul Friday Farms Inc. located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of moderate upright growth and a regular and productive bearer of peaches. The blossoms are contracted or partially spread when in full bloom. At the same time the petals of the blossoms are of lesser length than the length of petals of the normal showy blossom as exemplified by the Loring peach.

The blossoms of the present peach tree at full bloom may be characterized as being partially showy; i.e., neither non-showy such as the Redhaven or showy such as the Loring peach blossom. More specifically, the blossoms of the present peach tree have radially projecting and angularly spaced five blossom petals projecting upwardly at an inclined angle so as to form a blossom having a diameter of about ¾ measured across the blossoms. This partially showy blossom is in contrast to the showy blossom of the Loring peach type wherein the blossom petals are substantially flat and the diametrical measurement across the free outer edges of the petals is about 1-7/16". The typical non-showy blossom as exemplified for example by the Redhaven peach has five (5) radially extending and angularly spaced petals projecting upwardly at a relatively steep inclined angle so that the diametrical measurement across the outer edges of the petals is about ½".

The flesh of the fruit of the present peach tree is firm and is yellow.

The skin is smooth and is of dark color over about eighty (80%) percent of its surface at maturity. The red color occurs over about sixty (60%) percent of the surface about 10 days prior to maturity. At maturity the peach is substantially spheroidal with the diameter ranging between about 2½ to 3 inches.

The fruit has a firm flesh and may be described as resilient to the extent that the flesh is yieldable and restorable to its original state when subjected to impact forces which may cause permanent deformaties in peaches of the commercial varieties. The firmness of the fruit facilitates handling and packaging of the peaches without damaging the same for shipment. This results in less spoilage and also increases the shelf life.

The fruit matures in the latter part of the peach growing season of Southwestern Michigan. The fruit as mentioned heretofore is of red color over about eighty (80%) percent of its spheroidal surface and has a very attractive appearance.

BRIEF DESCRIPTION OF THE PHOTOGRAPHS

The accompanying photographic illustrations show a typical specimen of the fruit and the foliage of the new variety, with the upper and lower surface of the leaves and an exterior and sectional view of the fruit with the stone removed. The illustrations were taken shortly after being picked at maturity (firm ripe) and the colors as nearly true as reasonably possible in a photographic color representation.

The second photograph illustrates the flowers and buds of the P.F. 17 peach tree along with the flowers and buds of the P.F. 23 peach tree described in applicant's co-pending application, Ser. No. 07/726,251 filed Jul. 5, 1991 concurrently herewith and the flowers and buds of the Loring peach tree and the Red Haven peach tree.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree:
- *Height.*—Unpruned, 19'.
- *Width.*—Unpruned, 10'.
- *Size.*—Medium-large.
- *Vigor.*—Medium vigor terminal growth of 1 to 4 per year.
- *Density.*—Medium pruning requirements heavy.
- *Form.*—Upright.
- *Production.*—Productive, approximately ½ of the fruit annually.
- *Bearer.*—Consistent.
- *Disease resistance to bacterial leaf and fruit spot.*—Very good.

Trunk:
- *Size.*—Medium-to stocky.
- *Surface.*—Smooth to medium shaggy.

Branches:
- *Size.*—Medium.
- *Surface.*—Smooth to medium.
- *Lenticels.*—Medium number and medium size.
- *Color.*—Grayish brown.

Leaves:
- *Size.*—Large — Average length 6½" to 7". Average width — 1¾".
- *Form.*—Lanceolate — pointed.
- *Thickness.*—Medium.
- *Texture.*—Medium.
- *Margin.*—Serrate.
- *Peticole.*—Medium length-medium thickness.
- *Gland.*—Number varies from 1-4. Average 3. Located on base of leaf and upper portion of petiole.
- *Color.*—Upper surface: green (350c). surface: dull green (349c).

Flower buds:
- *Size.*—Medium.
- *Length.*—Medium.

Flowers:
- *Blooming period.*—Apr. 7, 1990 to Apr. 14, 1990.
- *Size.*—Medium or partially showy petal pattern (about ¾ inch diameter).
- *Pollen.*—Present, self-fertilizing.
- *Color.*—Pink.

Fruit:
- *Maturity when described.*—Firm ripe.
- *Date of first picking.*—Aug. 23, 1990 (About 15 days after picking Redhaven — Aug. 8, 1990. Fruit matures very evenly and can be picked in two pickings.).
- *Date of last picking.*—Aug. 27, 1990.
- *Size.*—Large sphere. Average diameter — 2¾".
- *Form.*—Spherical.
- *Suture.*—Very shallow.

Skin:
- *Thickness.*—Medium.
- *Texture.*—Tough, tenacious to skin.
- *Tendency to crack.*—None.
- *Down.*—Moderate to little.
- *Color.*—Yellow ground color (134c). Nearly overspread (80%) with red (174c) to (173c).

Flesh:
- *Texture.*—Firm similar to a cling peach.
- *Ripens.*—Relatively even.
- *Flavor.*—Good.
- *Aroma.*—Pleasant.
- *Eating quality.*—Excellent.
- *Color.*—Yellow (14c) to (13c). Pit cavity grayish yellow (15c).

Stone:
- *Type.*—Freestone.
- *Size.*—Average length — 1½". Average width — ¾". Average thickness — ½".
- *Form.*—Ovid.
- *Base.*—Straight.
- *Apex.*—Pointed.
- *Sides.*—Nearly equal.
- *Surface.*—Irregularly furrowed.
- *Color.*—Brown to reddish brown.
- *Tendency to crack.*—None.

Use: Desert.
Shipping quality: Good.
Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct varity of peach tree substantially as illustrated and described as large size, vigorous and upright in growth and a regular and productive bearer of large size, yellow flesh freestone fruit with good flavor and eating quality; and being further characterized by a partially showy blossom of about ¾" diameter when in full bloom, said fruit at maturity being of substantially spheroidal shape with firm flesh and a red skin color cover 80% of the fruit, said maturity occurring about 15 days after maturity of the Redhaven peach.

* * * * *

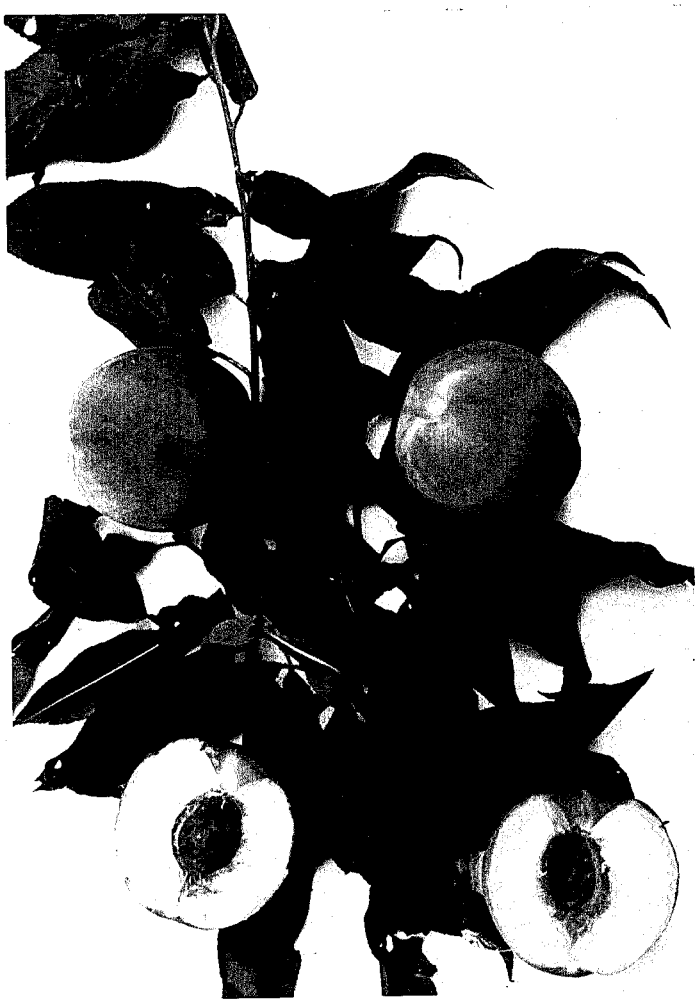

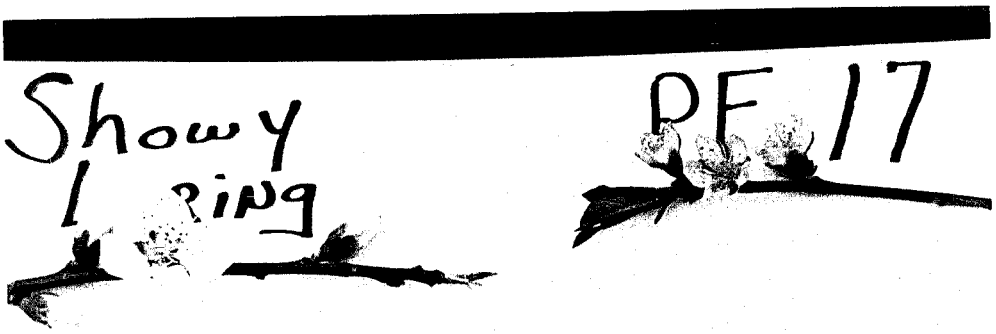
Showy
Spring
P.F. 17
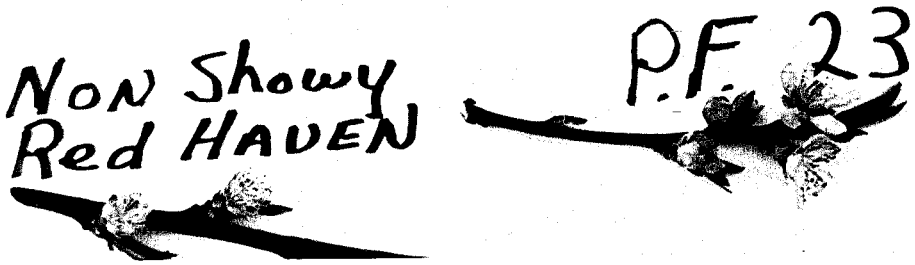
Non Showy
Red HAVEN
P.F. 23